(12) United States Patent
Connor (10) Patent No.: US 11,957,814 B2
(45) Date of Patent: Apr. 16, 2024

(54) ADIPOSE TISSUE MATRICES (71) Applicant: LifeCell Corporation, Madison, NJ (US)

(72) Inventor: Jerome Connor, Westminster, CO (US)

(73) Assignee: LifeCell Corporation, North Chicago, IL (US)

( * ) Notice: Subject to any disclaimer, the term of this patent is extended or adjusted under 35 U.S.C. 154(b) by 0 days.

(21) Appl. No.: 16/189,468

(22) Filed: Nov. 13, 2018

(65) Prior Publication Data

US 2019/0076582 A1 Mar. 14, 2019

Related U.S. Application Data (63) Continuation of application No. 13/483,674, filed on May 30, 2012, now abandoned.

(60) Provisional application No. 61/491,787, filed on May 31, 2011.

(51) Int. Cl.
| | | |
|---|---|---|
| *A61L 27/58* | (2006.01) | |
| *A61K 35/35* | (2015.01) | |
| *A61L 27/36* | (2006.01) | |
| *A61L 27/56* | (2006.01) | |
| *C12N 5/00* | (2006.01) | |
| *C12N 5/077* | (2010.01) | |

(52) U.S. Cl.
CPC .............. *A61L 27/58* (2013.01); *A61K 35/35* (2013.01); *A61L 27/3604* (2013.01); *A61L 27/3633* (2013.01); *A61L 27/3683* (2013.01); *A61L 27/56* (2013.01); *C12N 5/0068* (2013.01); *C12N 5/0653* (2013.01); *A61L 2430/04* (2013.01); *A61L 2430/34* (2013.01); *A61L 2430/40* (2013.01); *C12N 2533/90* (2013.01); *C12N 2537/10* (2013.01)

(58) Field of Classification Search
CPC .............. H01L 24/97; B29C 2793/009; B29C 47/0066; B29C 47/0023; B29C 47/003; B28B 17/0027; B29K 2021/00
See application file for complete search history.

(56) References Cited

U.S. PATENT DOCUMENTS

| | | |
|---|---|---|
| 4,233,969 A | 11/1980 | Lock et al. |
| 4,373,519 A | 2/1983 | Errede et al. |
| 4,569,348 A | 2/1986 | Hasslinger |
| 4,703,108 A | 10/1987 | Silver et al. |
| 4,950,483 A | 8/1990 | Ksander et al. |
| 5,149,331 A | 9/1992 | Ferdman et al. |
| 5,263,971 A | 11/1993 | Hirshowitz et al. |
| 5,298,015 A | 3/1994 | Komatsuzaki et al. |
| 5,336,616 A | 8/1994 | Livesey et al. |
| 5,364,756 A | 11/1994 | Livesey et al. |
| 5,437,651 A | 8/1995 | Todd et al. |
| 5,549,584 A | 8/1996 | Gross |
| 5,636,643 A | 6/1997 | Argenta et al. |
| 5,645,081 A | 7/1997 | Argenta et al. |
| 5,993,844 A | 11/1999 | Abraham et al. |
| 6,071,267 A | 6/2000 | Zamierowski |
| 6,135,116 A | 10/2000 | Vogel et al. |
| 6,345,623 B1 | 2/2002 | Heaton et al. |
| 6,553,998 B2 | 4/2003 | Heaton et al. |
| 6,814,079 B2 | 11/2004 | Heaton et al. |
| 6,840,960 B2 | 1/2005 | Bubb |
| 6,933,326 B1 | 8/2005 | Griffey et al. |
| 7,070,584 B2 | 7/2006 | Johnson et al. |
| 7,198,046 B1 | 4/2007 | Argenta et al. |
| 7,498,040 B2 | 3/2009 | Masinaei et al. |
| 7,498,041 B2 | 3/2009 | Masinaei et al. |
| 7,700,819 B2 | 4/2010 | Ambrosio et al. |
| 7,763,769 B2 | 7/2010 | Johnson et al. |
| 8,110,216 B2 | 2/2012 | Ambrosio et al. |
| 8,152,783 B2 | 4/2012 | Swain |
| 8,163,974 B2 | 4/2012 | Ambrosio et al. |
| 8,197,551 B2 | 6/2012 | Swain et al. |
| 8,197,806 B2 | 6/2012 | Girouard et al. |
| 8,257,372 B2 | 9/2012 | Swain et al. |
| 8,267,918 B2 | 9/2012 | Johnson et al. |
| 2002/0120185 A1 | 8/2002 | Johnson |
| 2002/0193448 A1 | 12/2002 | Wallace et al. |
| 2003/0035843 A1 | 2/2003 | Livesey et al. |
| 2003/0044444 A1 * | 3/2003 | Malaviya ................ A61L 27/56 424/423 |
| 2003/0143207 A1 | 7/2003 | Livesey et al. |
| 2003/0225347 A1 | 12/2003 | Argenta et al. |
| 2005/0028228 A1 | 2/2005 | McQuillan et al. |
| 2005/0043819 A1 | 2/2005 | Schmidt et al. |
| 2005/0159822 A1 | 7/2005 | Griffey et al. |
| 2006/0073592 A1 | 4/2006 | Sun et al. |
| 2006/0127375 A1 | 6/2006 | Livesey et al. |
| 2006/0153816 A1 | 7/2006 | Brown et al. |
| 2006/0210960 A1 | 9/2006 | Livesey et al. |
| 2007/0179607 A1 * | 8/2007 | Hodorek ............. A61F 2/30965 623/14.12 |
| 2007/0219471 A1 | 9/2007 | Johnson et al. |
| 2007/0248575 A1 | 10/2007 | Connor et al. |
| 2008/0027542 A1 | 1/2008 | McQuillan et al. |
| 2008/0114277 A1 | 5/2008 | Ambrosio et al. |

(Continued)

FOREIGN PATENT DOCUMENTS

| | | |
|---|---|---|
| WO | 1990/00060 A1 | 1/1990 |
| WO | 2002/40630 A2 | 5/2002 |

(Continued)

OTHER PUBLICATIONS

Argenta et al., Vacuum-assisted closure: a new method for wound control and treatment: clinical experience. Ann Plast Surg. Jun. 1997;38(6):563-76.

(Continued)

*Primary Examiner* — Michael B. Pallay
(74) *Attorney, Agent, or Firm* — McCarter & English, LLP (57) ABSTRACT

The present disclosure provides tissue products produced from adipose tissues, as well as methods for producing such tissue products. The tissue products can include acellular extracellular matrices. In addition, the present disclosure provides systems and methods for using such products.

18 Claims, 10 Drawing Sheets

(56) References Cited

U.S. PATENT DOCUMENTS

| | | |
|---|---|---|
| 2009/0035289 A1 | 2/2009 | Wagner et al. |
| 2009/0157017 A1 | 6/2009 | Ambrosio |
| 2009/0198167 A1 | 8/2009 | Ambrosio |
| 2009/0220579 A1* | 9/2009 | Hassingboe ............ A61L 15/32 424/445 |
| 2009/0287181 A1 | 11/2009 | Kagan |
| 2009/0326515 A1 | 12/2009 | Kagan |
| 2010/0040687 A1 | 2/2010 | Pedrozo et al. |
| 2010/0168689 A1 | 7/2010 | Swain et al. |
| 2010/0168720 A1 | 7/2010 | Swain et al. |
| 2010/0168870 A1 | 7/2010 | Swain et al. |
| 2010/0179515 A1 | 7/2010 | Swain et al. |
| 2011/0184357 A1 | 7/2011 | Robinson et al. |
| 2011/0251566 A1 | 10/2011 | Zimnitsky et al. |
| 2011/0293667 A1* | 12/2011 | Baksh ................ A61L 27/3633 424/400 |

FOREIGN PATENT DOCUMENTS

| | | |
|---|---|---|
| WO | 2011/019822 A2 | 2/2011 |
| WO | WO-2011019822 A2 * | 2/2011 ............ A61K 31/00 |

OTHER PUBLICATIONS

Blackburn et al., Negative-pressure dressings as a bolster for skin grafts. Ann Plast Surg. May 1998;40(5):453-7.

Brandi et al., Treatment with vacuum-assisted closure and cryo-preserved homologous de-epidermalised dermis of complex traumas to the lower limbs with loss of substance, and bones and tendons exposure. J Plast Reconstr Aesthet Surg. Dec. 2008;61(12):1507-11.

Chariker et al., Effective management of incisional and cutaneous fistulae with closed suction wound drainage. Contemporary Surgery. Jun. 1989;34:59-63.

Chinn et al., Closed wound suction drainage. J Foot Surg. Jan.-Feb. 1985;24(1):76-81.

Choi et al., Decellularized extracellular matrix derived from human adipose tissue as a potential scaffold for allograft tissue engineering. J Biomed Mater Res A. Jun. 1, 2011;97(3):292-9.

Choi et al., Fabrication of porous extracellular matrix scaffolds from human adipose tissue. Tissue Eng Part C Methods. Jun. 2010;16(3):387-96.

Dagalakis et al., Design of an artificial skin. Part III. Control of pore structure. J Biomed Mater Res. Jul. 1980;14(4):511-28.

Dattilo et al., Medical Textiles: Application of an Absorbable Barbed Bi-directional Surgical Suture. Journal of Textile and Apparel, Technology and Management. 2002 Spring;2(2):1-5.

Defranzo et al., Vacuum-assisted closure for the treatment of abdominal wounds. Clin Plast Surg. Apr. 2006;33(2):213-24.

Flack et al., An economic evaluation of VAC therapy compared with wound dressings in the treatment of diabetic foot ulcers. J Wound Care. Feb. 2008;17(2):71-8.

Griffey et al., Particulate dermal matrix as an injectable soft tissue replacement material. J Biomed Mater Res. 2001;58(1):10-5.

Ju et al., Beneficial effect of hydrophilized porous polymer scaffolds in tissue-engineered cartilage formation. J Biomed Mater Res B Appl Biomater. Apr. 2008;85(1):252-60.

KCI Licensing, Inc., V.A.C.® Therapy Safety Information. 4 pages, (2007).

Masters, Reliable, inexpensive and simple suction dressings. Br J Plast Surg. Apr. 1998;51(3):267.

O'Brien et al., The effect of pore size on cell adhesion in collagen-GAG scaffolds. Biomaterials. Feb. 2005;26(4):433-41.

O'Connor et al., Vacuum-assisted closure for the treatment of complex chest wounds. Ann Thorac Surg. Apr. 2005;79(4):1196-200.

Randall et al., Use of an acellular regenerative tissue matrix in combination with vacuum-assisted closure therapy for treatment of a diabetic foot wound. J Foot Ankle Surg. Sep.-Oct. 2008;47(5):430-3.

Wei et al., Construction of varying porous structures in acellular bovine pericardia as a tissue-engineering extracellular matrix. Biomaterials. May 2005;26(14):1905-13.

Wu et al., An Injectable Adipose Matrix for Soft Tissue Reconstruction. Plastic and Reconstructive Surgery Advance Online Article. DOI: 10.1097/PRS.0b013e31824ec3dc. 33 pages, (2012).

Wu et al., Preparation of collagen-based materials for wound dressing. Chin Med J (Engl). Mar. 2003;116(3):419-23.

Xu et al., A porcine-derived acellular dermal scaffold that supports soft tissue regeneration: removal of terminal galactose-alpha-(1,3)-galactose and retention of matrix structure. Tissue Eng Part A. Jul. 2009;15(7):1807-19.

Yang et al., A cartilage ECM-derived 3-D porous acellular matrix scaffold for in vivo cartilage tissue engineering with PKH26-labeled chondrogenic bone marrow-derived mesenchymal stem cells. Biomaterials. May 2008;29(15):2378-87.

International Search Report and Written Opinion for Application No. PCT/US2012/039969, dated Jul. 30, 2012.

* cited by examiner

ADIPOSE TISSUE MATRICES

This application is a continuation of U.S. application Ser. No. 13/483,674, filed May 30, 2012, which claims priority under 35 U.S.C. § 119 to U.S. provisional application No. 61/491,787, filed on May 31, 2011, which is incorporated herein by reference in its entirety.

The present disclosure relates to tissue products, and more particularly, to extracellular tissue matrices made from adipose tissue.

Various tissue-derived products are used to regenerate, repair, or otherwise treat diseased or damaged tissues and organs. Such products can include tissue grafts and/or processed tissues (e.g., acellular tissue matrices from skin, intestine, or other tissues, with or without cell seeding). Such products generally have properties determined by the tissue source (i.e., tissue type and animal from which it originated) and the processing parameters used to produce the tissue products. Since tissue products are often used for surgical applications and/or tissue replacement or augmentation, the products should support tissue growth and regeneration, as desired for the selected implantation site. The present disclosure provides adipose tissue products that can allow improved tissue growth and regeneration for various applications.

SUMMARY

According to certain embodiments, methods for producing tissue products are provided. The methods include selecting an adipose tissue; mechanically processing the adipose tissue to reduce the tissue size; and treating the mechanically processed tissue to remove substantially all cellular material from the tissue. The processed tissue is suspended in a solution and cross-linked to produce a stable three-dimensional structure.

In addition, tissue products made by the disclosed processes are provided. The processes can include selecting an adipose tissue; mechanically processing the adipose tissue to reduce the tissue size; and treating the mechanically processed tissue to remove substantially all cellular material from the processed tissue. In addition, the processes can include suspending the processed tissue in a solution and cross-linking the tissue to produce a stable three-dimensional structure.

In addition, adipose tissue products are provided. The products can include a decellularized adipose extracellular tissue matrix, wherein the tissue matrix has been formed into a predetermined three-dimensional shape, and wherein the tissue matrix is partially cross-linked to maintain the three-dimensional shape.

Furthermore, methods of treatment are provided. The methods can comprise placing a negative pressure manifold on a wound wherein the manifold comprises a decellularized adipose extracellular tissue matrix. The tissue matrix is formed into a predetermined three-dimensional shape and is partially cross-linked to maintain the three-dimensional shape. A drape is placed over the manifold to seal the wound, and a negative pressure is applied to draw fluid through the manifold.

DESCRIPTION OF CERTAIN EXEMPLARY EMBODIMENTS

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Various human and animal tissues can be used to produce products for treating patients. For example, various tissue products for regeneration, repair, augmentation, reinforcement, and/or treatment of human tissues that have been damaged or lost due to various diseases and/or structural damage (e.g., from trauma, surgery, atrophy, and/or long-term wear and degeneration) have been produced. Such products can include, for example, acellular tissue matrices, tissue allografts or xenografts, and/or reconstituted tissues (i.e., at least partially decellularized tissues that have been seeded with cells to produce viable materials).

A variety of tissue products have been produced for treating soft and hard tissues. For example, ALLODERM® and STRATTICE™ are two dermal acellular tissue matrices made from human and porcine dermis, respectively. Although such materials are very useful for treating certain types of conditions, materials having different biological and mechanical properties may be desirable for certain applications. For example, ALLODERM® and STRATTICE™ have been used to assist in treatment of structural defects and/or to provide support to tissues (e.g., for abdominal walls or in breast reconstruction), and their strength and biological properties make them well suited for such uses. However, such materials may not be ideal for regeneration, repair, replacement, and/or augmentation of adipose-containing tissues. Accordingly, the present disclosure provides tissue products that are useful for treatment of adipose-containing tissues as wells as other tissue sites. The present disclosure also provides methods for producing such tissue products.

The tissue products can include adipose tissues that have been processed to removal at least some of the cellular components. In some cases, all, or substantially all cellular material is removed, thereby leaving adipose extracellular matrix proteins. In addition, the products can be processed to remove some or all of the extracellular and/or intracellular lipids. As described further below, the extracellular matrix proteins can be further treated to produce a three-dimensional porous, or sponge-like material. In addition, to allow treatment of a selected tissue site, the material can be further processed (e.g., by cross-linking) to form a stable structure.

As noted, the tissue products of the present disclosure are formed from adipose tissues. The adipose tissues can be derived from human or animal sources. For example, human adipose tissue can be obtained from cadavers. In addition, human adipose tissue could be obtained from live donors (e.g., with an autologous tissue). Adipose tissue may also be obtained from animals such as pigs, monkeys, or other sources. If animal sources are used, the tissues may be further treated to remove antigenic components such as 1,3-alpha-galactose moieties, which are present in pigs, but not humans or primates. In addition, the adipose tissue can be obtained from animals that have been genetically modified to remove antigenic moieties. See Xu, Hui. et al., "A Porcine-Derived Acellular Dermal Scaffold that Supports Soft Tissue Regeneration: Removal of Terminal Galactose-α-(1,3)-Galactose and Retention of Matrix Structure," Tissue Engineering, Vol. 15, 1-13 (2009), which is incorporated by reference in its entirety.

Figure 1:
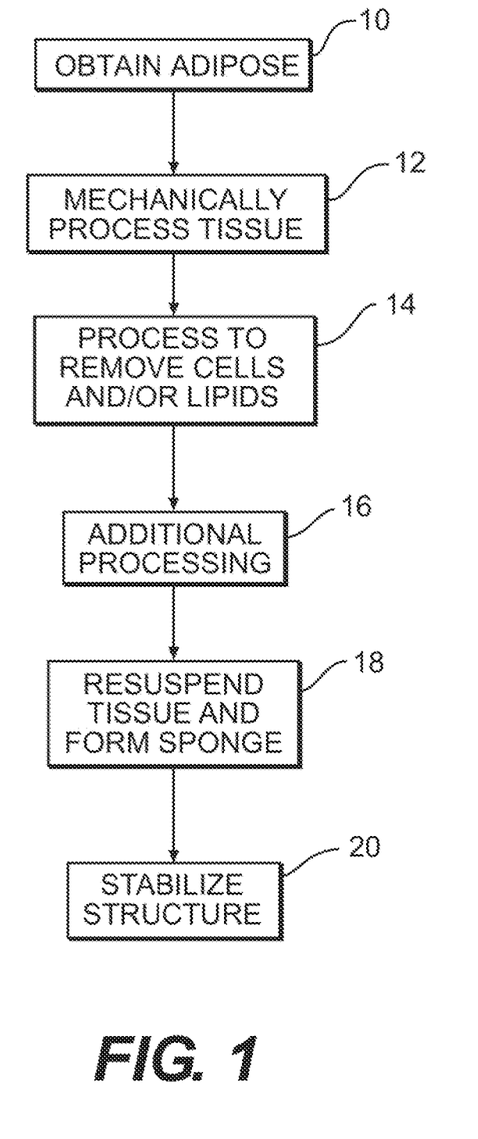
FIG. 1 is a flow chart illustrating a process for producing adipose tissue products, according to certain embodiments.

An exemplary process for producing the tissue products of the present disclosure is illustrated in FIG. 1. As shown, the process generally includes obtaining adipose tissue (Step 10); mechanically processing the adipose tissue to produce small pieces (Step 12); further processing the tissue to remove substantially all cellular material and/or lipids from the tissue (Step 14); resuspending the tissue in a solution to form a porous matrix or sponge (Step 16); and cross-linking the tissue to produce a stable three-dimensional structure (Step 18). Each of these steps is explained in more detail below.

To assist in removal of the cellular components and produce a flowable mass, the tissue is first processed to produce small pieces. In various embodiments, the material is cut, ground, blended or otherwise mechanically treated to reduce the size of the tissue and/or to form a putty or flowable material. The adipose tissue can be treated using any repetitive cutting, grinding, or blending process. For example, in one embodiment, the tissue is first cut into relatively small pieces (e.g., about 2 cm×2 cm). The pieces can them be placed in an aqueous solution, which is treated with a blade grinder or similar instrument.

After processing, the tissue is then treated to removal cellular components and lipids. The cellular material can be removed by washing the material. For example, in some embodiments, the material is further diluted with water or another solvent. The diluted material is then centrifuged, and free lipids and cell debris will flow to the top, while the extracellular matrix proteins are deposited as a pellet. The protein pellet can then be resuspended, and the washing and centrifugation can be repeated until a sufficient amount of the lipids and cellular materials are removed. In some cases, the process is repeated until substantially all cellular material and/or lipids are removed.

During, before, and/or after the washing steps, additional solutions or reagents can be used to process the material. For example, enzymes, detergents, and/or other agents may be used in one or more steps to remove cellular materials or lipids, remove antigenic materials, and/or reduce the bacteria or other bioburden of the material. For example, one or more washing steps can be included using detergents such as sodium dodecylsulfate or TRIS to assist in cell and lipid removal. In addition, enzymes such as lipases, DNAses, RNAses, alpha-galactosidase, or other enzymes can be used to ensure destruction of nuclear materials, antigens from xenogenic sources, and/or viruses. Further, peracetic acid solutions and/or peroxides can be used to help remove cellular materials and destroy bacteria or other potentially infectious agents.

After removal of cellular components, the material can then be formed into a porous or sponge-like material. Generally, the extracellular matrix is first resuspended in an aqueous solvent. A sufficient amount of solvent is used to allow the material to form a liquid mass that can be poured into a mold having the size and shape of the desired tissue product. The amount of water added can be varied based on the desired porosity of the final material. In some cases, the resuspended extracellular matrix may be mechanically treated by grinding, cutting, blending or other processes one or more additional times, and the treated material can be centrifuged and resuspended one or more times to further remove cellular material or lipids (if needed) and/or to control the viscosity of the extracellular matrix.

Once any additional washing and grinding steps are complete, the resuspended material is placed in a container or mold to form the porous, sponge-like product. Generally, the porous or sponge-like material is formed by drying the material to leave a three-dimensional matrix with a porous structure. In some embodiments, the material is freeze-dried. Freeze-drying can allow production of a three-dimensional structure that generally conforms to the shape of the mold.

The specific freeze drying protocol can be varied based on the solvent used, sample size, and/or to optimize processing time. One suitable freeze-drying process can include freezing the material to −35° C. over a 45 minute period; holding the samples at −35° C. for 90 minutes to insure complete freezing; applying a vacuum; raising the temperature to −10° C. and holding for 24 hours; raising the temperature to 0° C. and holding for 24 hours; and raising the temperature to 20° C. and holding for 12 hours. The freeze-dried samples can then be removed from the freeze-dryer and packaged in foil pouches under nitrogen.

After forming the porous, sponge-like material, the tissue can be treated so that it forms a stable three-dimensional shape. For example, generally, a mechanically processed tissue, when formed into a porous matrix, may form a more putty- or paste-like material when it is implanted in a body, becomes wet, or is placed in a solution. Therefore, the desired shape and size may be lost. In addition, the porous structure, which may be important for supporting cell attachment, tissue growth, vascular formation, and tissue regeneration, may be lost. Accordingly, the material should be further processed to stabilize the size, shape, and structure of the material.

In some embodiments, the material is cross-linked. In some embodiments, the material is cross-linked after freeze drying. However, the material could also be cross-linked before or during the freeze-drying process. Cross-linking can be performed in a variety of ways. In one embodiment, cross-linking is accomplished by contacting the material with a cross-linking agent such as glutaraldehyde, genepin, carbodiimides, and diisocyantes. In addition, cross-linking can be performed by heating the material. For example, in some embodiments, the material can be heated to between 70° C. to 120° C., or between 80° C. and 110° C., or to about 100° C., or any values between the specified ranges in a reduced pressure or vacuum. In addition, other cross-linking processes may be used to produce any of the disclosed products, including ultraviolet irradiation, gamma irradiation, and/or electron beam irradiation. In addition, a vacuum is not needed but may reduce cross-linking time. Further, lower or higher temperatures could be used as long as melting of the matrix proteins does not occur and/or sufficient time is provided for cross-linking.

In various embodiments, the cross-linking process can be controlled to produce a tissue product with desired mechanical, biological, and/or structural features. For example, cross-linking may influence the overall strength of the material, and the process can be controlled to produce a desired strength. In addition, the amount of cross-linking can affect the ability of the product to maintain a desired shape and structure (e.g., porosity) when implanted. Accordingly, the amount of cross-linking can be selected to produce a stable three-dimensional shape when implanted in a body, when contacted with an aqueous environment, and/or when compressed (e.g., by surrounding tissues or materials).

Excessive cross-linking may change the extracellular matrix materials. For example, excessive cross-linking may damage collagen or other extracellular matrix proteins. The damaged proteins may not support tissue regeneration when the tissue products are placed in an adipose tissue site or other anatomic location. In addition, excessive cross-linking can cause the material to be brittle or weak. Accordingly, the amount of cross-linking may be controlled to produce a desired level of stability, while maintaining desired biological, mechanical, and/or structural features.

Exemplary cross-linking processes can include contacting a freeze-dried material, produced as discussed above, with glutaraldehyde. For example, a 0.1% glutaraldehyde solution can be used, and the tissue can be submerged in the solution for about for 18 hours followed by extensive rinsing in water to remove the solution. Alternatively, or in combination, a dehydrothermal process can be used. For example, one exemplary dehydrothermal process includes treating the material at 100° C. and ~20 inches of Hg for 18 hour, followed by submersion in water. The final cross-linked tissue products can be stored in a film pouch.

As discussed above, the tissue products should have the ability to support cell ingrowth and tissue regeneration when implanted in or on a patient. In addition, the tissue products should have the ability to act as a carrier for and support the growth of cells, including stems cell, such as adipose-derived stem cells. Accordingly, the processes discussed above should not alter the extracellular matrix proteins (e.g., by damaging protein structure and/or removing important glycosaminoglycans and/or growth factors). In some embodiments, the products will have normal collagen banding as evidenced by transmission electron microscopy.

In various embodiments, the tissue products are treated with a process that retains either or both of the native hyaluronic acid and chondroitin sulfate. Accordingly, the tissue products can include either or both of hyaluronic acid and chondroitin sulfate. In addition, the process can be selected to maintain native growth factors. For example, the tissue products can be produced such that the tissue products contains one or more growth factors selected from PECAM-1, HGF, VEGF, PDGF-BB, follistatin, IL-8, and FGF-basic.

Use of Tissue Products

The tissue products described herein can be used to treat a variety of different anatomic sites. For example, as discussed throughout, the tissue products of the present disclosure are produced from adipose tissue matrices. Accordingly, it is believed that the adipose tissue products will provide superior regenerative capabilities when implanted in certain tissue sites, as compared to materials produced from other tissue types. In some cases, the tissue products can be implanted in tissue sites that are predominantly or significantly adipose tissue. In some cases, the tissue sites can include a breast (e.g., for augmentation, replacement of resected tissue, or placement around an implant). In addition, any other adipose-tissue containing site can be selected. For example, the tissue products may be used for reconstructive or cosmetic use in the face, buttocks, abdomen, hips, thighs, or any other site where additional adipose tissue having structure and feel that approximates native adipose may be desired. In any of those sites, the tissue may be used to reduce or eliminate wrinkles, sagging, or undesired shapes.

When used for breast tissue replacement or augmentation, the tissue can provide advantages over other tissue products. For example, although some tissue products allow ingrowth and tissue formation, those products may form significant fibrotic tissue that does not mimic normal breast texture and feel, and appears abnormal on radiologic imaging. Since the tissue products of the present disclosure are formed from adipose, they may support more normal regeneration of adipose tissue.

The tissue products disclosed herein can also be formed into thin films for use as adhesion barriers, coverings, wraps, and the like. For example, a sample of adipose tissue can be placed on a flat surface, and a second flat surface can be placed on top of the sample. In some embodiments, force is applied (e.g., by applying pressure or adding weight to the second surface) sufficient to flatten the sample of adipose tissue to a thickness of about 1.5 mm or less (e.g., about 1.5, 1.4, 1.3, 1.2, 1.1, 1.0, 0.9, 0.8, 0.7, 0.6, 0.5, 0.4, 0.3, 0.2, 0.1, or 0.05 mm, or any value in between). Alternatively, a roller (e.g., a pasta roller) can be used to apply pressure and flatten the sample of adipose tissue. In some embodiments, an absorbant material on the flat surface or roller can be used to wick away moisture from the adipose tissue as it is being flattened.

The adipose tissue films disclosed herein may retain some or all of the collagen, growth factors, and/or other biological molecules found in the adipose tissue prior to film preparation. The film may also provide a flexible material having a malleability similar to cellophane. In some embodiments, the application of pressure to generate a film material compresses the collagen fibers in the tissue product, thereby increasing the mechanical strength of the tissue product (e.g., as a result of the bundling, condensing, and/or intertwining of the collagen fibers in the film). In certain embodiments, after the film is prepared, the film can be cross-linked (e.g., using chemical crosslinking agents, dihydrothermal treatment, irradiation, and/or any other crosslinking method known to one of skill in the art). Crosslinking the adipose film may serve to further increase its mechanical strength (e.g., by increasing its ability to handle tensional, torsional, and/or other forces without tearing or breaking).

Film tissue products may be used as adhesion barriers. In some embodiments, the densely packed collagen network of the compressed film may prevent cells or fibrous tissue (e.g., scar tissue) from repopulating on, or passing through, the film. For example, a film of adipose tissue may be wrapped around a temporary implant to prevent the build-up of undesirable cells or fibrous tissue on the implant, thereby hindering subsequent removal of the implant. Similarly, a film may be placed between two or more static tissues where it is desirable to prevent the tissues from joining or adhering to each other.

Film tissue products may also be used as coverings or wraps. For example, a film tissue product could be wrapped around an artery, vein, a tendon or ligament to protect the artery, vein, tendon, or ligament (e.g., as part of a ligament repair or transplant procedure). In this example, the film could serve to protect the artery, vein, tendon, or ligament from abrasion and/or to increase the strength of the artery, vein, tendon or ligament. Similarly, a film tissue product may be placed over or around a suture line to protect the line from damage (e.g., to protect suture lines against tearing caused by abrasion or other forces imposed on the sutures). Likewise, film tissue products could be used to protect a surgically-prepared anastomosis (e.g., an arterial or other blood vessel anastomosis, an anastomosis associated with intestinal resection, etc.). In these embodiments, a thin film product, comprising biological material, may provide an advantage in allowing for non-bulky wrapping of a surgical site with a bioresorbable and biocompatible material. In these embodiments, it may also be desirable to cross-link the film tissue product to increase structural strength and the ability to handle tensional, torsional, or other forces without tearing or breaking.

The tissue products described herein can also be used in conjunction with negative pressure therapy systems, such as the VAC® system, which is produced by Kinetic Concepts, Inc. Such systems can be used to treat a variety of tissues sites and include, for example, a negative pressure source such as a pump and one or more treatment materials, which often include a porous foam or manifold. General examples of such systems are described in U.S. Patent Publication Number, 2010/0040687 A1, which was filed on Aug. 13, 2009. The products may be used when implanted or placed on or near a wound or other surgical site since the tissue products can allow a sustained manifolding of pressure, which is needed for negative pressure therapy.

Accordingly, the present disclosure also provides for systems for treatment of tissue comprising one or more tissue products and a negative pressure therapy system. The negative pressure therapy system can include a negative pressure source, e.g., a pump, and a fluid connection source (e.g., tube or conduit for connecting the negative pressure source to the tissue product). In addition, the systems can include a flexible sheet or other mechanism to seal a wound or other surgical site to be treated. For example, in some embodiments, the system can include a thin flexible sheet of material that is placed over a treatment site. The sheet can be configured to seal the treatment site using an adhesive or other connection system, and the fluid connection can pass into or near the treatment site to produce a negative pressure within the treatment site.

Further, the tissue products can be used as carriers for cells. For example, the products can be implanted in any of the sites or used as discussed above, but can also be seeded with cells. In some cases, the cells can include stem cells such as adipose-derived stem cells. In addition, other pluripotent cells may be use, as well as cells from any tissue source (e.g., blood, bone marrow, fetal stem cells, cord blood cells, etc.). The cells can be seeded onto the tissue after implantation or before implantation. In addition, the cells may be cultured on the tissue product before implantation and then be implanted in or on a body.

Figure 10:
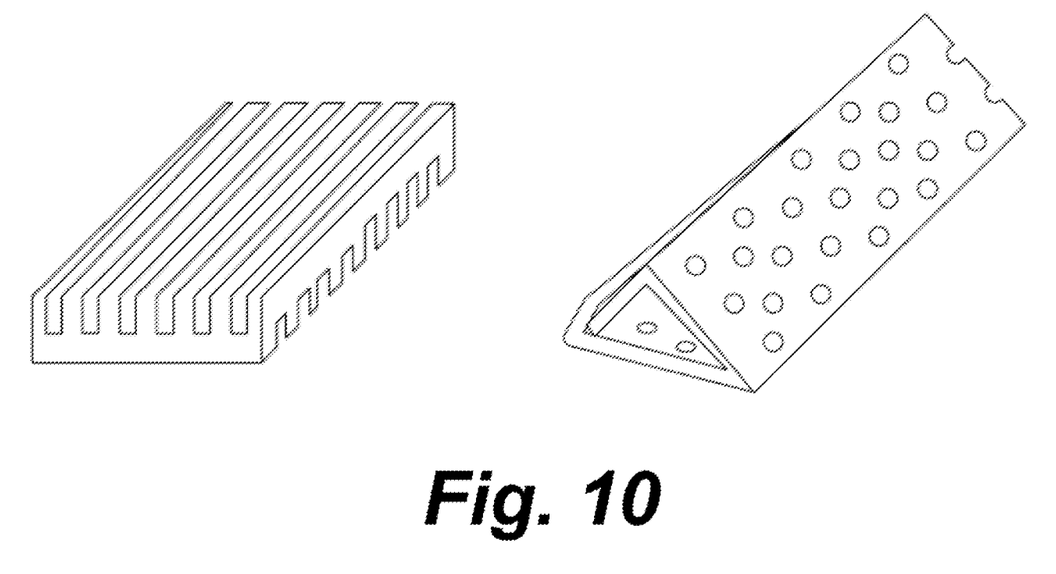
FIG. 10 shows two examples of adipose tissue-based drain manifolds. The exemplary manifolds contain grooves (left) and holes (right).

The adipose tissue products of the present disclosure can also be used as drains and/or drain manifolds. For example, adipose tissue products can be cut and/or otherwise shaped to form a tube, column, sheet, or any other desired shape for use as a drain or drain manifold. In some embodiments, a tissue product is shaped to have a cross-section having at least one dimension of up to about 5 mm (e.g., a dimension of about 5, 4, 3, 2, or 1 mm, or any value in between). In certain embodiments, the tissue product has a length of up to about 20 cm (e.g., about 1, 5, 10, 15, or 20 cm, or any length in between). In some embodiments, the tissue product has grooves, channels, and/or holes added to it. In some embodiments, the grooves, channels, and/or holes constitute up to about 70% (e.g., about 70, 60, 50, 40, 30, 20, or 10%, or any percentage in between) of the surface area of the tissue product and allow for the passage of fluids and/or pressure through the drain or manifold. Examples of this type of drain manifold are shown in FIG. 10.

Alternatively, in various embodiments, an adipose tissue product can be cut into thin strips and rolled to form a drain in the shape of a tube or other desired shape. In some embodiments, the thin strips have a thickness of up to about 2 mm (e.g., about 0.5, 1.0, 1.5, or 2.0 mm, or any value in between), a width of up to about 20 mm (e.g., about 1, 5, 10, 15, or 20 mm, or any value in between), and a length of about 20 cm (e.g., about 1, 2, 3, 4, 5, 10, 15, or 20 cm, or any value in between). In some embodiments, the rolled tube of adipose tissue comprises a hollow tube. In some embodiments, the rolled tube has grooves, channels, and/or holes carved in it. In some embodiments, the grooves, channels, and/or holes allow for the passage of fluids and/or pressure through the manifold.

Adipose tissue drains and/or drain manifolds can be implanted in a patient to provide channel(s) to bring negative pressure to an implant site and/or to remove blood or other fluids from the implant site. In some embodiments, the drain and/or manifold is implanted to prevent the formation of seromas and/or hematomas following a surgical procedure. In some embodiments, the manifold is implanted to provide for adequate drainage, e.g., after a surgical procedure such as a tumor removal, abdominal surgery, breast implant or other plastic surgery. In some embodiments, the adipose tissue drain and/or manifold is used in conjunction with negative pressure therapy systems, such as the VAC® system, which is produced by Kinetic Concepts, Inc., as described above. In various embodiments, the adipose tissue products provide biocompatible and bioresorbable drains and/or drain manifolds. In some embodiments, the implanted adipose tissue drain and/or drain manifold can be repopulated with native cells from tissue surrounding an implant site, thereby avoiding the need to remove the drain and/or manifold at the completion of a drainage procedure.

EXAMPLES

The following examples serve to illustrate, and in no way limit, the present disclosure.

A. Processing of Adipose Tissue

Human adipose tissue was obtained from cadaveric sources following all of the requirements of the American Association of Tissue Banks (AATB). Full thickness samples containing dermis and fat were obtained from AATB certified tissue banks. The adipose tissue was mechanically excised from the dermis and was placed in buffered saline and held at 4° C. until processing.

The adipose tissue, of various thicknesses, was cut into small pieces of approximately 2 cm×2 cm using scissors. The adipose pieces were suspended in water at a ratio of 1-g of adipose to 2-ml of water. Next, 150-ml of the suspension was then minced using a blade grinder (RETSCH® GRINDMASTER GM200) for three minutes at 10,000-rpm at room temperature. The grinding process was repeated until all of the adipose pieces had been minced.

The minced adipose suspension was further diluted at a 1:1 ratio with water, and the final mixture was centrifuged at 2500× g for 5 minutes The free lipid and cell debris floated to the top and were expressed off. The adipose-derived extracellular matrix proteins (ECM) formed a pellet, and the pellet fraction was retained. The centrifugation and pelleting were repeated until all materials were processed. All of the ECM pellets were combined, resuspended in water, and washed by centrifugation three times.

The washed adipose ECM was resuspended in water at a ratio of 50 ml of ECM to 100 ml of water and was minced using the blade grinder for 2 minutes at 10,000-rpm at room temperature. The suspension was washed using centrifugation as described above. The final ECM suspension was centrifuged at 3500× g for 10 minutes to generate a final packed ECM pellet. The washed ECM pellet was slowly resuspended in water at a ratio of 1-ml of ECM to 2-ml of water to generate an adipose ECM slurry.

B. Production of Adipose ECM Sponge

The slurry was dispersed into 8 cm×8 cm molds. The molds were placed in a standard industrial freeze-dryer and subjected to freeze-drying according to the following procedure. The ECM slurry was frozen to −35° C. over a 45-min period. The samples were held at −35° C. for 90 minutes to insure complete freezing. The vacuum was then initiated in the system. The shelf temperature was raised to −10° C. and held for 24 hours. The temperature was then raised to 0° C. and held for 24 hours. Finally, the temperature was raised to 20° C. and held for 12 hours. The freeze-dried ECM samples were removed from the freeze-dryer and packaged in foil pouches under nitrogen.

C. Cross-linking of Adipose ECM Sponges

The freeze-dried ECM products were cross-linked by two methods. The first was chemical cross-linking using glutaraldehyde, and the second was biophysical cross-linking using dehydrothermal treatment.

C(1). Glutaraldehyde Cross-linking

The adipose sponge was removed from the foil pouch and placed in a glass dish containing an excess of 0.1% glutaraldehyde solution prepared in water. The sponge was held submerged until the sample was completely hydrated. The sponge was incubated in the 0.1% glutaraldehyde solution for 18 hours followed by extensive rinsing in water to remove the glutaraldehyde solution. The final cross-linked adipose sponge was stored in a film pouch.

C(2). DHT Cross-linking

The adipose sponge was removed from the foil pouch and placed in a vacuum oven and subjected to a temperature of 100° C. and ~20 inches of Hg for 18 hours. Following the dehydrothermal treatment, the sponge was hydrated by submersion in water. The final cross-linked adipose sponge was stored in a film pouch.

Figure 2A:
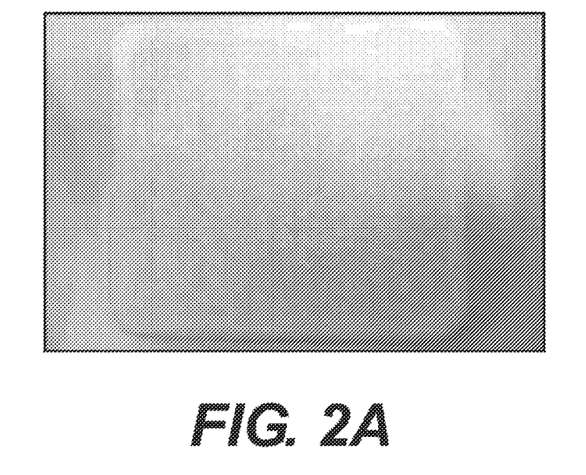
FIGS. 2A-2D are macroscopic images of adipose tissue products produced according to various embodiments.
Figure 2B:
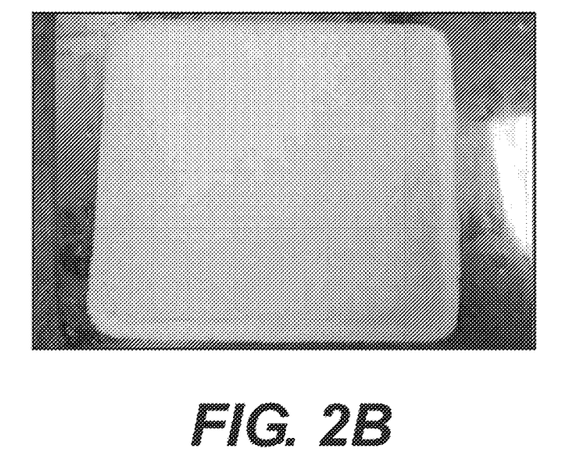

FIGS. 2A-2D are macroscopic images of adipose tissue products produced according to various embodiments. FIG. 2A is an adipose tissue product that was cross-linked with glutaraldehyde, as described in C(1) above, in a hydrated state. FIG. 2B is an adipose tissue product that was cross-linked with glutaraldehyde, as described in C(2) above, and has been squeezed to remove most water.

Figure 2C:
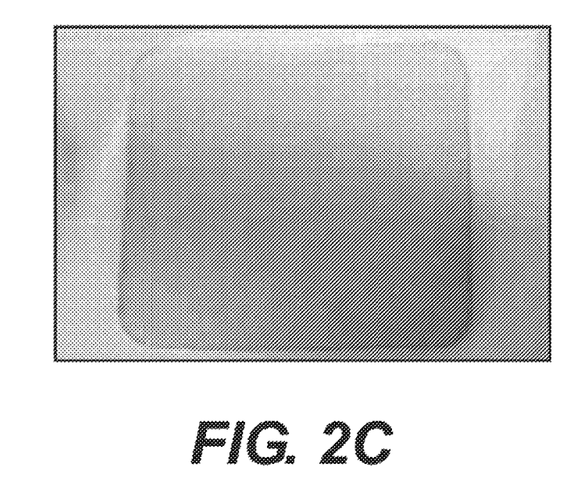
Figure 2D:
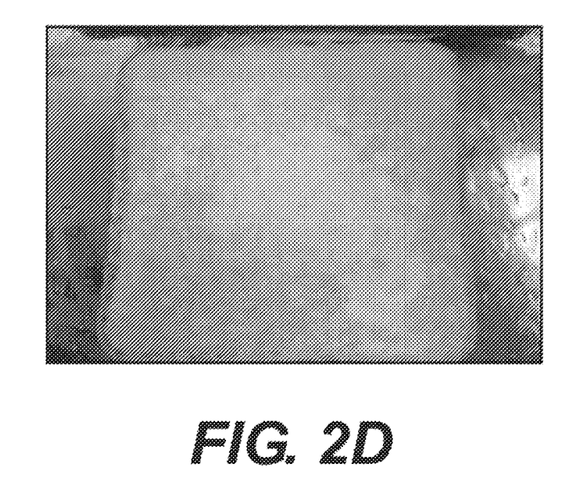
Figure 3A:
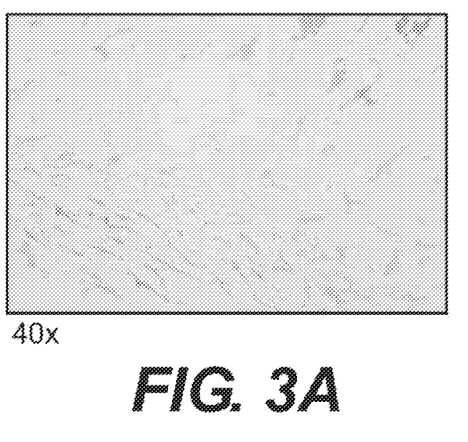
FIGS. 3A-3D are hematoxylin and eosin stained sections of adipose tissue products produced according to various embodiments.
Figure 3B:
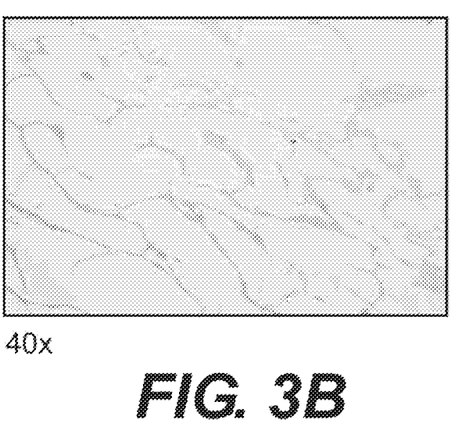
Figure 3C:
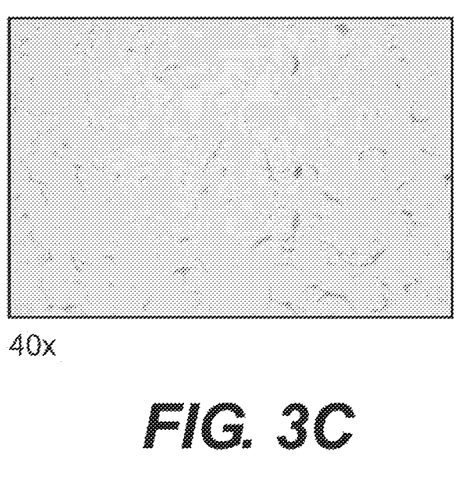
Figure 3D:
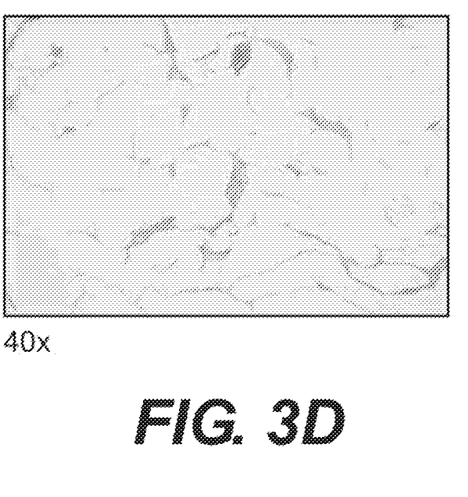

FIGS. 2C-2D are hematoxylin and eosin (H&E) stained sections of adipose tissue products produced according to various embodiments. FIG. 2C is an adipose tissue product that was cross-linked with the dehydrothermal process, as described in C(2) above, in a hydrated state. FIG. 2D is an adipose tissue product that was cross-linked with the dehydrothermal process, as described in C(2) above, and has been squeezed to remove most water.

The tissue products were subjected to a manifolding test whereby the material was placed in a vacuum port, and a negative pressure was applied to the material to determine if the material could act as a manifold for negative pressure therapy and/or would maintain a porous structure over time. The manifolding test demonstrated a sustained manifolding ability. Accordingly, the tissue products were found to maintain a porous structure even after contact with aqueous solutions. Therefore, the materials will be suitable for use in negative pressure treatment systems and will maintain a porous structure to allow tissue ingrowth and regeneration when implanted within a body.

Figure 4A:
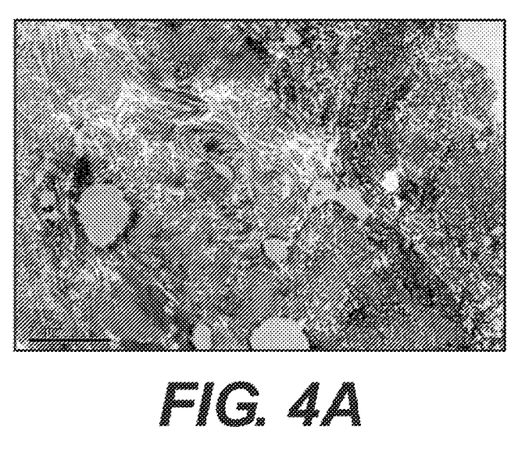
FIGS. 4A-4D are transmission electron micrographs of adipose tissue products produced according to various embodiments.
Figure 4B:
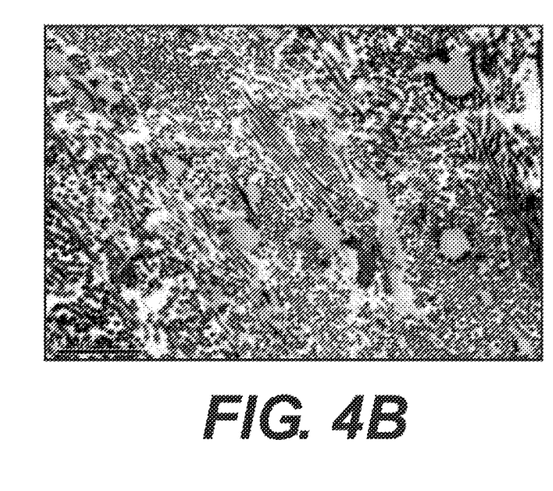
Figure 4C:
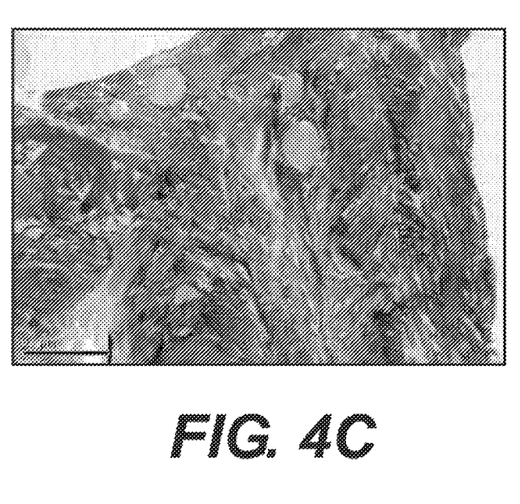
Figure 4D:
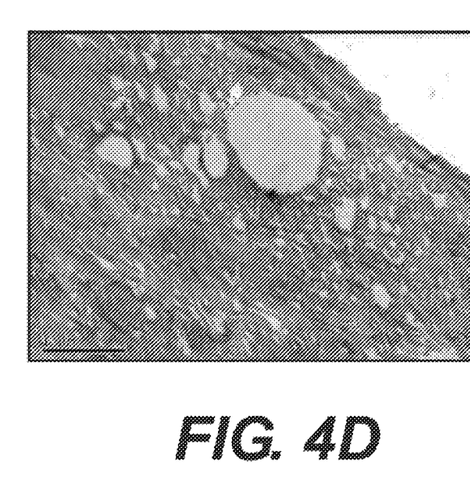
Figure 5A:
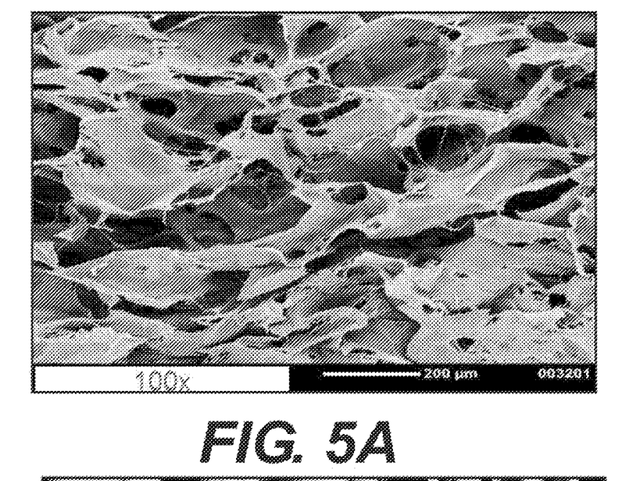
FIGS. 5A-5D are scanning electron microscope images of adipose tissue products produced according to various embodiments.
Figure 5B:
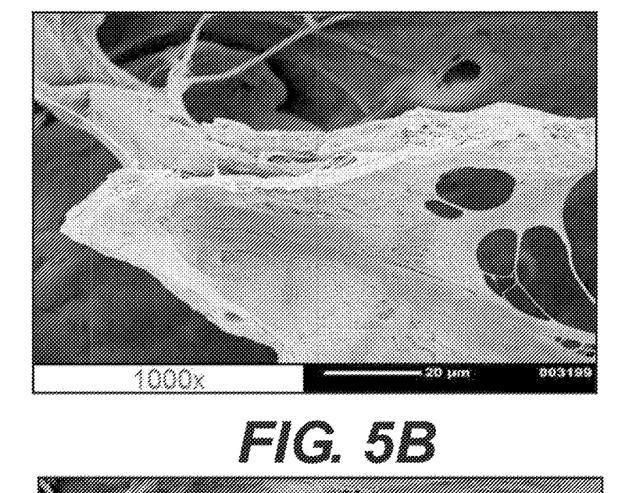
Figure 5C:
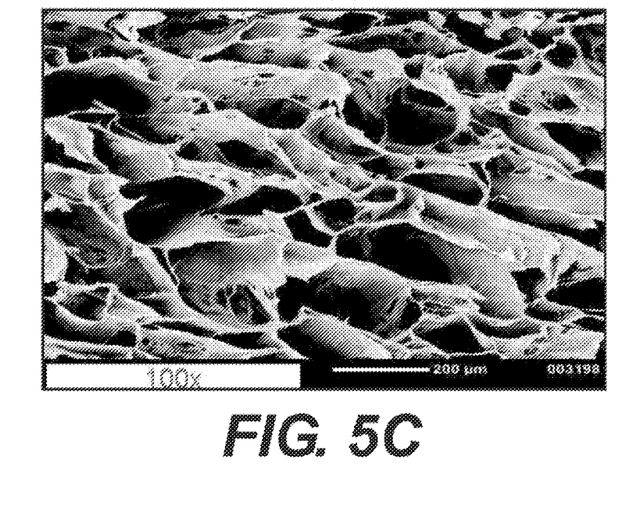
Figure 5D:
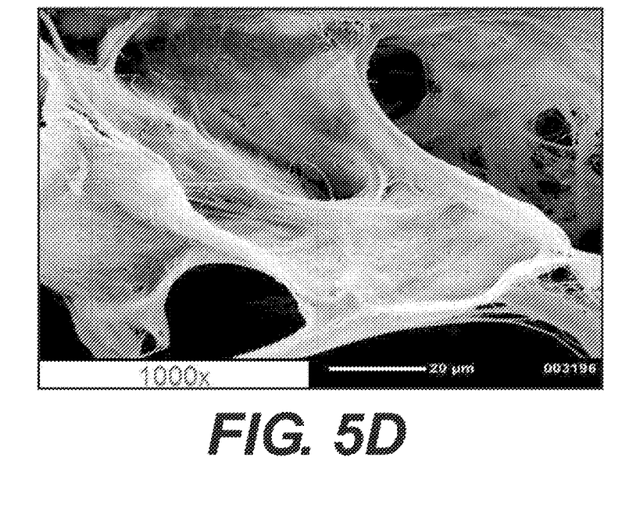

FIGS. 4A-4B are transmission electron micrographs of adipose tissue products produced with glutaraldehyde cross-linking, as described in C(1). FIGS. 5A-5B are scanning electron microscope images of the adipose tissue products produced with glutaraldehyde cross-linking, as described in C(1). FIGS. 4C-4D are transmission electron micrographs of adipose tissue products produced with dehydrothermal cross-linking, as described in C(2) above. FIGS. 5C-5D are scanning electron microscope images of the adipose tissue products produced with dehydrothermal cross-linking, as described in C(2) above. As shown, cross-linked adipose tissue products maintained an intact porous structure. The TEM images of FIGS. 4A-4D demonstrated normal collagen banding.

D. Animal Implant Study

Hydrated adipose sponges were subjected to e-beam irradiation at a dose of 15 to 18-kGy to achieve sterilization. The sterile sponge samples (n=4) (GA and DHT cross-linked) were implanted subcutaneously in nude rats for 21-days. The biopsies were harvested, processed for histology, and evaluated by a histopathologist to determine the biological response. Both sponge configurations were observed to have significant infiltration of native fibroblast cells, robust presence of new blood vessels, and evidence of newly deposited native collagen in the absence of a significant immune cell presence. The adipose sponges displayed positive evidence of biocompatibility.

Figure 6A:
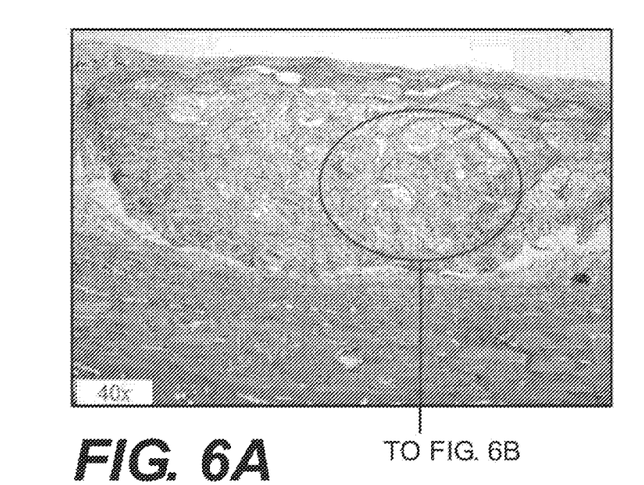
FIGS. 6A-6C are hematoxylin and eosin stained sections of adipose tissue products produced according to various embodiments after implantation in nude rats.
Figure 6B:
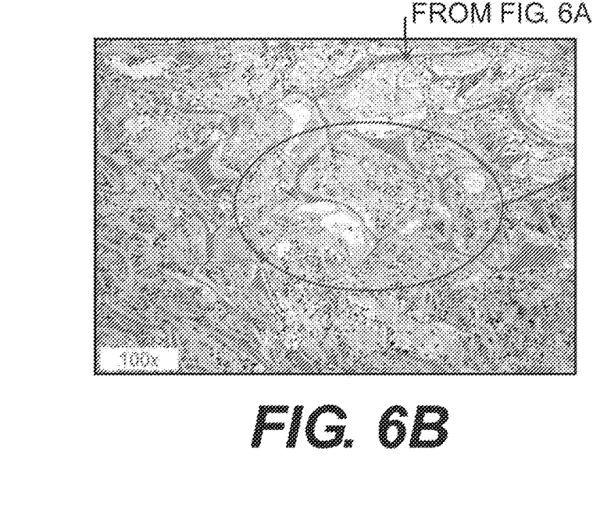
Figure 6C:
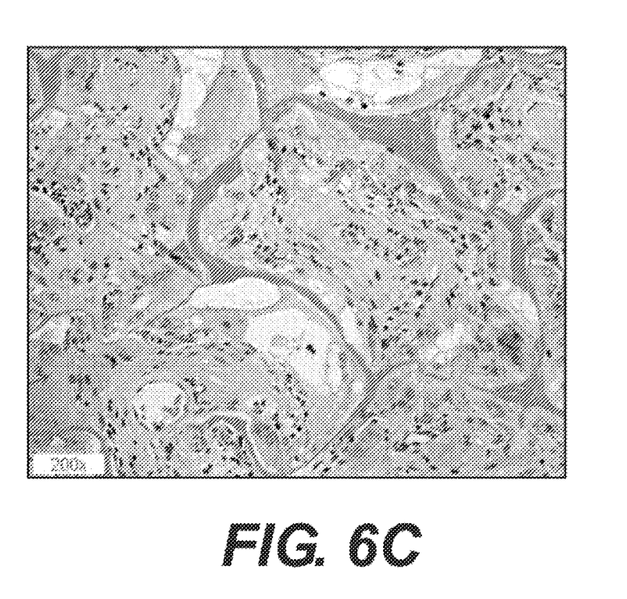
Figure 7A:
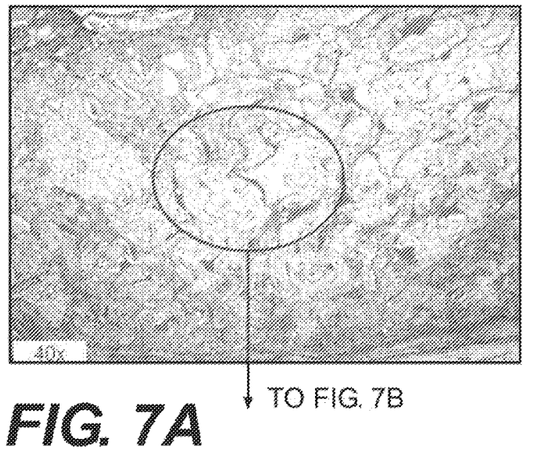
FIGS. 7A-7C are hematoxylin and eosin stained sections of adipose tissue products produced according to various embodiments after implantation in nude rats.
Figure 7B:
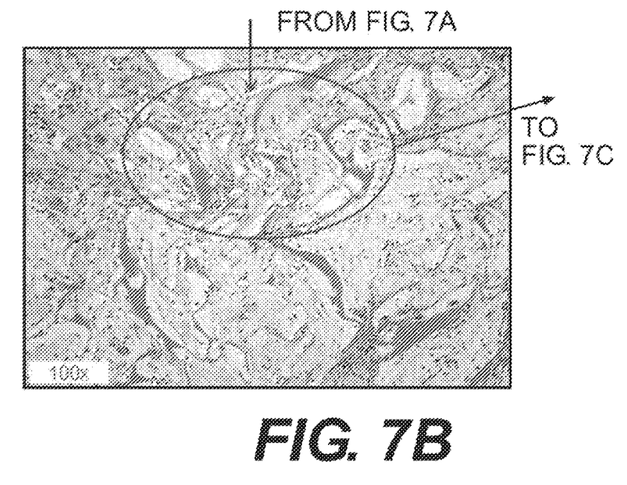
Figure 7C:
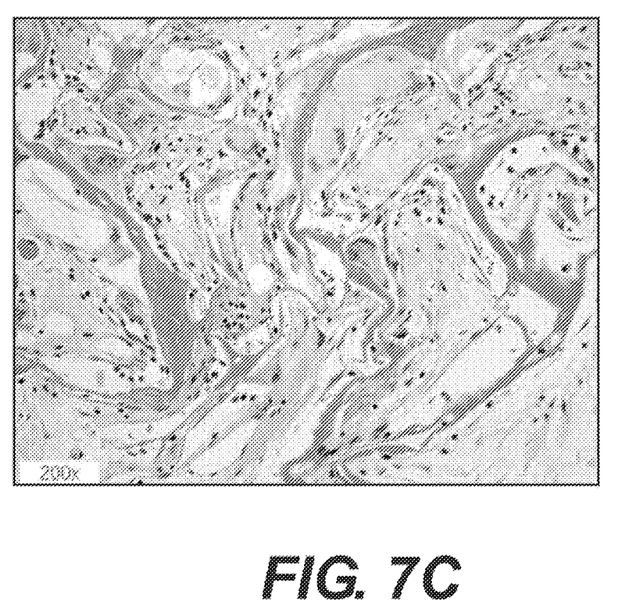
Figure 8A:
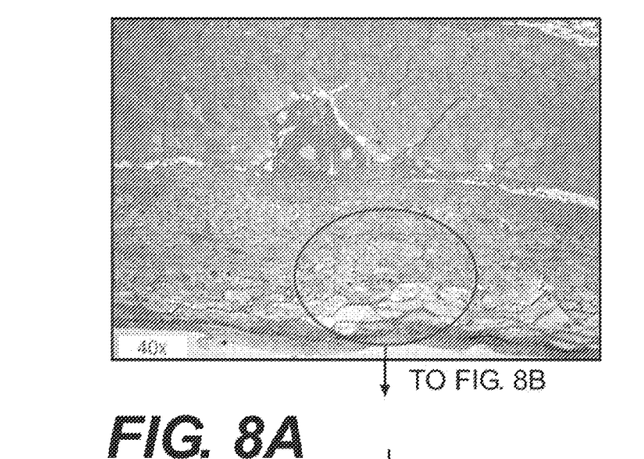
FIGS. 8A-8C are hematoxylin and eosin stained sections of adipose tissue products produced according to various embodiments after implantation in nude rats.
Figure 8B:
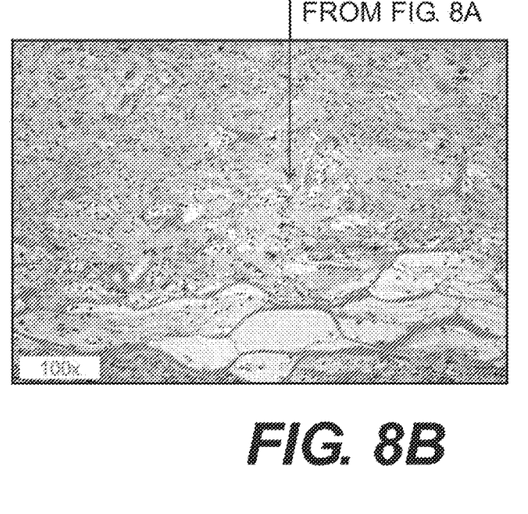
Figure 8C:
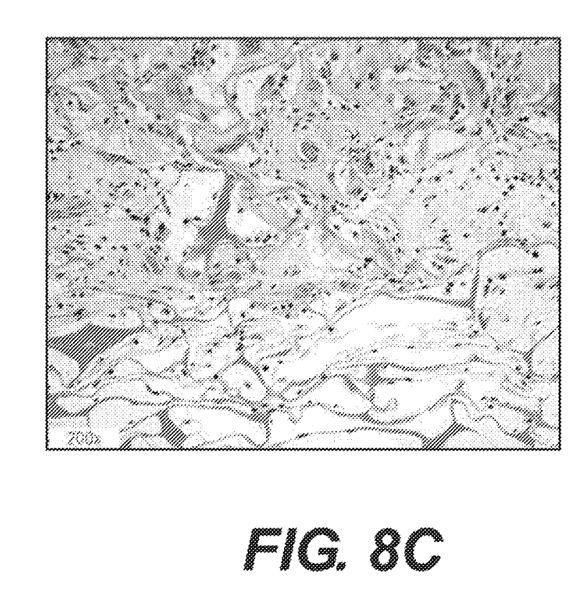
Figure 9A:
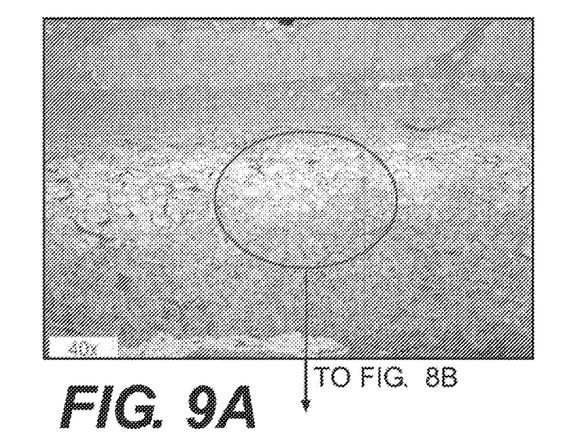
FIGS. 9A-9C are hematoxylin and eosin stained sections of adipose tissue products produced according to various embodiments after implantation in nude rats.
Figure 9B:
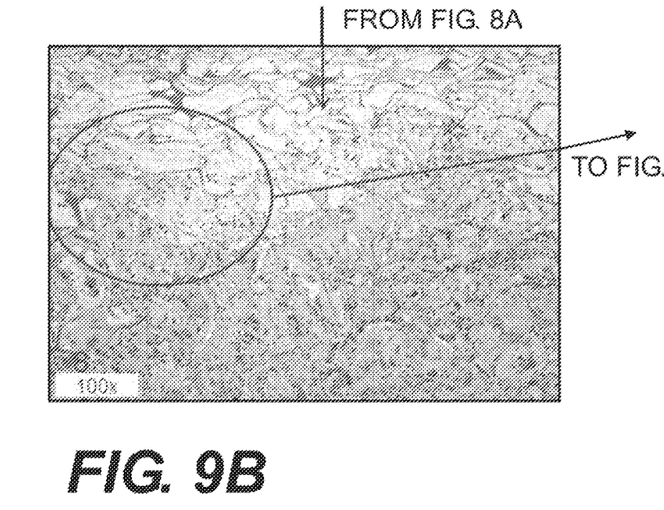
Figure 9C:
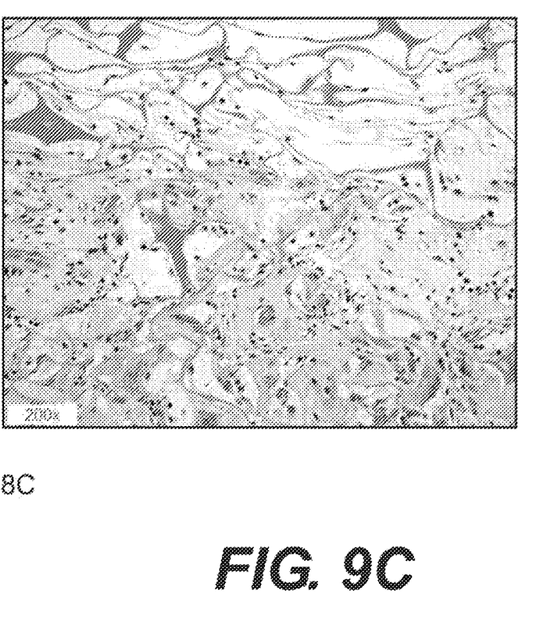

FIGS. 6A-6C are hematoxylin and eosin stained sections of adipose tissue products produced with glutaraldehyde cross-linking, as described in C(1) after implantation in nude rats. FIGS. 7A-7C are additional hematoxylin and eosin stained sections of adipose tissue products produced with glutaraldehyde cross-linking, as described in C(1) above, after implantation in nude rats. FIGS. 8A-8C are hematoxylin and eosin stained sections of adipose tissue products produced with dehydrothermal cross-linking, as described in C(2) above, after implantation in nude rats. FIGS. 9A-9C are hematoxylin and eosin stained sections of adipose tissue products produced with dehydrothermal cross-linking, as described in C(2) above, after implantation in nude rats.

Each of the glutaraldehyde and dehydrothermal cross-linked products demonstrated significant cellular infiltration, neo-vascularization, and new collagen formation. Accordingly, the tissue products are believed to be suitable for tissue regeneration when implanted in adipose-containing tissues or other tissue sites. The samples demonstrated modest inflammatory infiltrates.

The preceding examples are intended to illustrate and in no way limit the present disclosure. Other embodiments of the disclosed devices and methods will be apparent to those skilled in the art from consideration of the specification and practice of the devices and methods disclosed herein.

What is claimed is:

1. A tissue product, comprising:
a decellularized adipose extracellular tissue matrix, wherein the tissue matrix includes porcine acellular particulate adipose tissue matrix that has been formed into a sponge and then partially cross-linked by heating in a vacuum at a temperature range between 70 to 90 degrees Celsius to form a stable porous structure that retains the ability to regenerate adipose tissue when implanted in an adipose-containing tissue site.

2. The product of claim 1, wherein the tissue matrix has been processed to remove at least some lipids.

3. The product of claim 1, wherein the tissue matrix is freeze-dried.

4. The product of claim 1, wherein the tissue matrix maintains the porous structure, size, and shape of the sponge when implanted in a body.

5. The product of claim 1, wherein the tissue matrix maintains the porous structure, size, and shape of the sponge when contacted with an aqueous environment.

6. The product of claim 1, wherein the tissue matrix maintains the porous structure, size, and shape of the sponge when compressed.

7. The product of claim 1, wherein the tissue matrix contains hyaluronic acid and chondroitin sulfate.

8. The product of claim 1, wherein heating in a vacuum is performed at a temperature range between 70 to 85 degrees Celsius.

9. The product of claim 1, wherein heating in a vacuum is performed at a temperature range between 70 to 80 degrees Celsius.

10. A tissue product made by a process comprising:
selecting porcine adipose tissue;
mechanically processing the porcine adipose tissue to form particulate tissue;
treating the particulate tissue to remove substantially all cellular material from the tissue to produce acellular particulate tissue matrix;
suspending the acellular particulate tissue matrix in a solution;
drying the solution to form a porous sponge having a porous structure; and
partially cross-linking the sponge to stabilize the sponge, wherein cross-linking includes heating the sponge in a vacuum at a temperature range between 70 to 90 degrees Celsius.

11. The product of claim 10, wherein drying the solution comprises freeze-drying.

12. The product of claim 10, wherein the sponge is cross-linked such that the sponge maintains the porous structure, size, and shape of the sponge when contacted with an aqueous environment.

13. The product of claim 10, wherein the sponge is cross-linked such that the sponge maintains the porous structure, size, and shape of the sponge when implanted in a body.

14. The product of claim 10, wherein the sponge is cross-linked such that the sponge maintains the porous structure, size, and shape of the sponge when compressed.

15. The product of claim 10, wherein mechanically processing the tissue includes at least one of cutting, grinding, or blending to produce small particles.

16. The product of claim 10, wherein the tissue contains hyaluronic acid and chondroitin sulfate.

17. The product of claim 10, wherein heating in a vacuum is performed at a temperature range between 70 to 85 degrees Celsius.

18. The product of claim 10, wherein heating in a vacuum is performed at a temperature range between 70 to 80 degrees Celsius.

* * * * *